(12) United States Patent
Guibert et al.

(10) Patent No.: US 6,328,711 B1
(45) Date of Patent: Dec. 11, 2001

(54) CHEMO-THERMO APPLICATOR FOR CANCER TREATMENT

(75) Inventors: Raul Guibert, Brentwood, CA (US); Michael Ebert, New York, NY (US)

(73) Assignee: Vanny Corporation, Los Angeles, CA (US)

( * ) Notice: Subject to any disclaimer, the term of this patent is extended or adjusted under 35 U.S.C. 154(b) by 0 days.

(21) Appl. No.: 09/487,434

(22) Filed: Jan. 19, 2000

(51) Int. Cl.⁷ .................................................. A61M 29/00
(52) U.S. Cl. .................. 604/103.01; 604/101.02; 604/103.06; 604/509
(58) Field of Search ............................ 604/96.01, 103.01, 604/103.02, 103.08, 507, 514; 606/27, 190, 108, 194; 607/96, 104, 105, 107, 113

(56) References Cited

U.S. PATENT DOCUMENTS

| | | | |
|---|---|---|---|
| 2,734,508 | * 2/1956 | Kozinski | 607/105 |
| 4,398,535 | * 8/1983 | Guibert | 128/399 |
| 4,595,008 | * 6/1986 | Guibert | 128/399 |
| 4,708,718 | * 11/1987 | Daniels | 604/53 |
| 4,754,752 | * 7/1988 | Ginsburg et al. | 128/303.12 |
| 5,624,392 | * 4/1997 | Saab | 604/43 |
| 5,876,743 | * 3/1999 | Ibsen et al. | 424/426 |
| 6,149,574 | * 11/2000 | Trauthen et al. | 600/3 |

* cited by examiner

Primary Examiner—Richard K. Seidel
Assistant Examiner—Jennifer Maynard
(74) Attorney, Agent, or Firm—Hopgood, Calimatde, Judlowe & Mondolino, LLP

(57) ABSTRACT

A chemo-thermo applicator insertable into a tubular membrane in the body of an individual to occupy a site therein in which the surface of the membrane is disrupted by cancerous lesions. The applicator includes concentric inner and outer tubular balloons in which the annular space therebetween is filled with a chemotherapy supply the outer balloon being perforated. In operation, a stream of heated air is fed into the inner balloon which acts to inflate this balloon and to heat the supply to cause it to melt and form a cream. Inflation of the inner balloon acts to expand the outer balloon causing it to conform to the surface of the membrane. The pressure imposed on the supply as the inner balloon expands, forces the heated cream to extrude through the outer balloon perforations to coat the surface of the membrane with the heated cream which then functions as a chemo-thermo agent to destroy the cancerous lesions.

9 Claims, 2 Drawing Sheets

CHEMO-THERMO APPLICATOR FOR CANCER TREATMENT

BACKGROUND OF INVENTION

1. Field of Invention:

This invention relates generally to devices for treating cancer, and more particularly to an applicator for this purpose which synergistically combines the positive effects of hyperthermia and chemotherapy to destroy cancerous lesions.

2. Status of Prior Art:

It has long been recognized that by heating a malignant tumor to a higher temperature than that of tissues surrounding the tumor whose temperature is at normal body temperature, this action destroys the tumor. The effectiveness of such hyperthermia depends on the fact that cancers have poor circulation and a reduced ability to dissipate heat. Thus a temperature of no more than 115 degrees Fahrenheit is capable of destroying cancer cells while sparing healthy tissues.

The 1987 U.S. Pat. No. 4,398,537 to Guibert discloses a hyperthermia technique for destroying a malignant tumor whose site in the body of an individual is within an internal region underlying the surface of the skin. Applied to the surface of the skin is a stream of air which is heated to produce an air wave having periodic pulses whose peak temperature is well-above body temperature, the intervals between these pulses being at an air temperature just above body temperature.

As a consequence, heat from the high temperature pulses in the stream of air flowing over the surface of the skin is conductively transferred from the skin during the lower-temperature intervals to the tumor in the internal region below the skin, thereby raising the temperature of the tumor to a level which destroys it. But because the skin surface is subjected to relatively long low-temperature intervals between the high-temperature pulses, the cooling which takes place during these intervals results in a skin temperature which is never raised to an unsafe degree.

Also of prior art interest is the 1995 Guibert et al. U.S. Pat. No. 6,554,487. This patent discloses a combined chemo-thermo therapy technique in which a pharmaceutical agent, such as a lipolysis cream, is topically applied to a localized skin surface overlying a problem region to be treated. This surface is then subjected to an air stream whose temperature alternates periodically from a high peak level to a lower base level in a pulsatory heat energy wave pattern. Because heat transfer takes place under the skin in the intervals between successive peaks, the temperature of the problem region containing the tumor is significantly raised, but that on the skin surface remains at a tolerable level. As a consequence, the absorption of the agent and its diffusion throughout the tissue of the heated problem region is accelerated and its interaction therewith is promoted to enhance the effectiveness of the treatment.

The concern of the present invention is with the treatment of cancerous lesions disposed in an internal region of the body that is not accessible to hyperthermic apparatus of the type disclosed in the above-identified Guibert patents in which a stream of heated air is applied to a skin area overlying an internal region having a malignant tumor therein.

Typical of a region which is not accessible to the prior Guibert apparatus is the colon, for should there be malignant tumors on the mucosa of the colon, one could not then destroy these tumors by applying pulsed heat to a skin area of the body. The site of the colon in the body is so distant from the skin surface, that if a stream of heated air were applied to this skin surface, the heat in the course of its transfer from the skin surface to the colon would be dissipated in the intervening tissues of the body, and would never reach the colon.

The colon is a large intestine extending from the cecum to the rectum. Although the colon is a continuous hollow muscular tube, it is divided into several sections, namely the ascending colon, the transverse colon and the descending colon. As it enter the pelvis, the colon makes a double curve similar to the letter S, this being known as the sigmoid colon. The end of the sigmoid colon terminates at the rectum. The rectum and the colon constitute a meandering passage having a tubular membrane. In order therefore for an applicator or other device to reach a remote site in the tubular membrane of the colon, the applicator must snake its way through the passage. Thus a flexible fiberoptic sigmoidoscope can make its way well into the colon to detect cancerous tissues.

In the United States, the colon and rectum account for more cancer cases each year than any other anatomic site, other than the lungs. The primary treatment for colon cancer consists of a surgical resection of the lesions. But surgical treatment for colon cancer is not a permanent cure and often does not prevent a recurrence of the cancer.

According to the Merck Manual ($15^{th}$ Edition, page 819), chemotherapy has not proven to be effective as a surgical adjuvant in clinical trials of colon and rectal cancers. And studies of adjuvant radiation therapy, after curative cancer surgery, indicate that such radiation only delays the recurrence of the cancer.

SUMMARY OF INVENTION

In view of the foregoing, the main object of this invention is to provide a chemo-thermo applicator insertable in a tubular membrane within an individual to a site therein at which the surface of the membrane is disrupted by cancerous lesions, the applicator serving to destroy these lesions.

Among the significant advantages of an applicator in accordance with the invention are the following:

A. The applicator is capable of snaking its way into a meandering tubular membrane so that it can be placed at the site of the cancerous lesions to be destroyed.

B. In operation, the applicator synergistically combines the positive therapeutic effects of hyperthermia and chemotherapy to destroy there cancerous lesions.

C. The thermal energy applied by the applicator to the cancerous lesions is adjustable to attain optimal conditions of treatment without damaging healthy tissues.

Also an object of this invention is to provide an applicator of the above type which includes a tubular balloon whose diameter is such as to permit the applicator to easily pass through a meandering tubular membrane, which balloon when the applicator is at a desired site can then be expanded to engage the surface of the membrane.

Briefly stated, these objects are attained by an insertable into a tubular membrane in the body of an individual to occupy a site therein in which the surface of the membrane is disrupted by cancerous lesions. The applicator includes concentric inner and outer tubular balloons in which the annular space therebetween is filled with a chemotherapy supply, the outer balloon being perforated.

In operation, a stream of heated air is fed into the inner balloon which acts to inflate this balloon and to heat the supply to cause it to melt to form a cream. Inflation of the inner balloon acts to expand the outer balloon causing it to conform to the surface of the membrane. The pressure imposed on the supply as the inner balloon expands, forces the cream heated to extrude through the outer balloon perforations to coat the surface of the membrane with the heated cream which then functions as a chemo-thermo agent to destroy the cancerous lesions.

BRIEF DESCRIPTION OF DRAWING

For a better understanding of the invention as well as other objects and further features thereof, reference is made to the following detailed description to be read in conjunction with the accompanying drawings, wherein.

DESCRIPTION OF INVENTION

Figure 1:
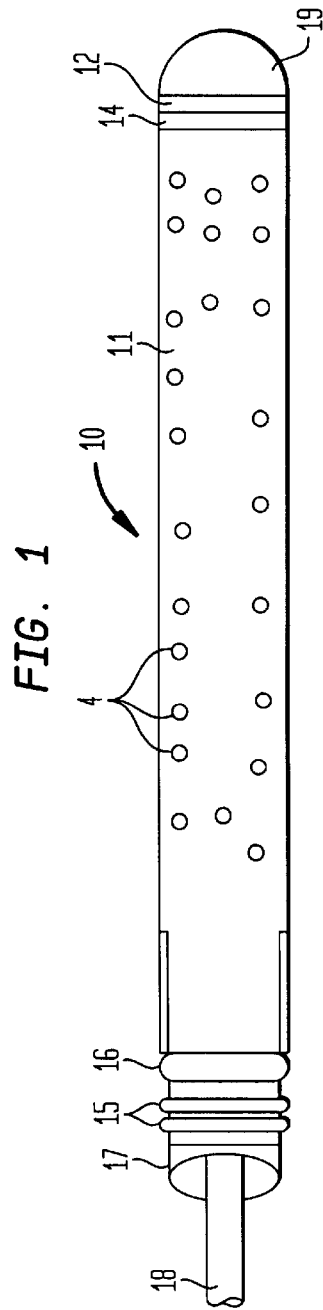
FIG. 1 illustrates a preferred embodiment of a chemo-thermo applicator in accordance with the invention in its uninflated state.
Figure 2:
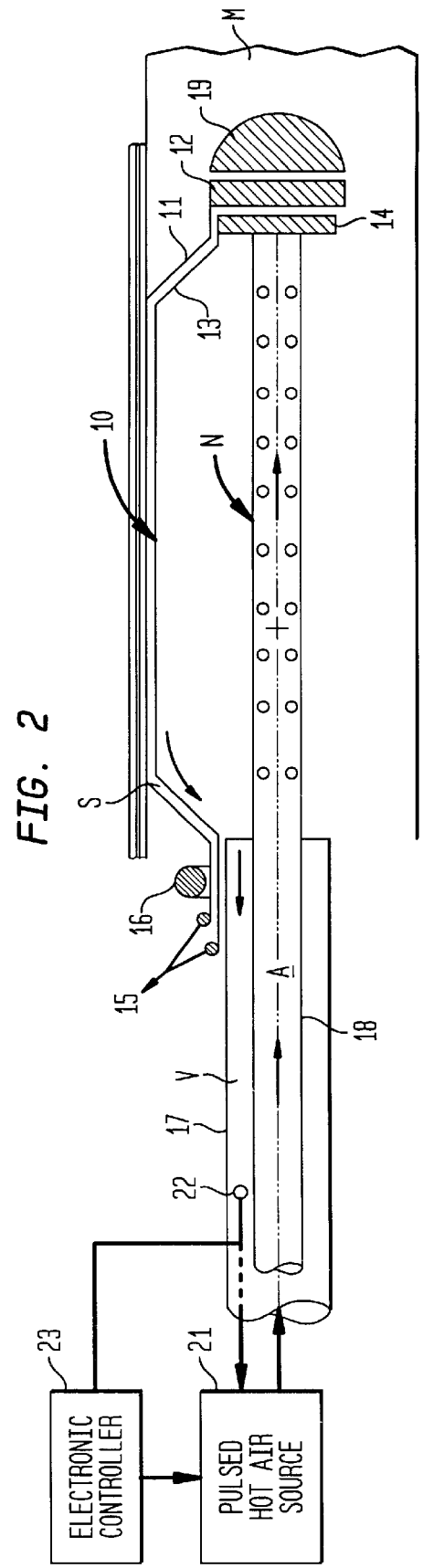
FIG. 2 is a section taken through the applicator in its inflated state within a tubular membrane in the body of an individual being treated.

Referring now to FIGS. 1 and 2, shown therein is a preferred embodiment of an applicator 10 in accordance with the invention. It includes an outer tubular balloon 11 that is condom-like, balloon 11 normally having a cylindrical shape of uniform diameter. Balloon 11 is circumferentially perforated to create small holes H that are uniformly distributed throughout the balloon.

Outer balloon 11 which is fabricated of stretchable latex or similar elastic material of good strength is bonded at its front end to an annular mounting disc 12 of the same diameter. Concentric with outer balloon 11 and formed of the same material is an inner balloon 13 is impervious to air, hence it is inflatable. Inner balloon is which of somewhat smaller diameter then outer balloon 11 is bonded to an annular mounting disc 14 of the same diameter.

The narrow annular space S between concentric balloons 11 and 13 has deposited therein a supply of an anti-cancer thermotherapy agent that is appropriate to the cancer that is to be treated by the applicator; such as an anti-tumor antibiotic, a plant alkaloid or an antimetabolite agent.

At body temperature, the chemotherapy agent in supply S is in a semi-solid state. But when heated to a temperature level that is effective in destroying cancerous lesions (say 120 degrees F.) it then softens and melts to form a cream that can be extruded through holes H in the outer balloon.

Figure 5:
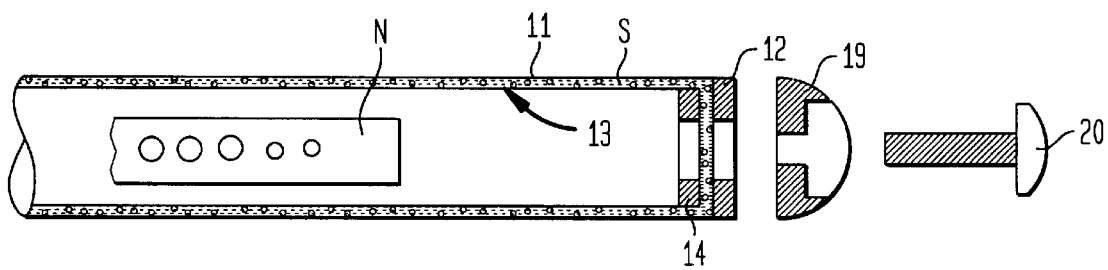
FIG. 5 illustrates how to assemble the applicator.

To assemble the applicator, a plastic nose piece 19 is joined to the annular mounting discs 12 and 14 of the outer and inner balloons 11 and 13 by a plug 20 as shown in FIG. 5.

Telescoped into the rear ends of the concentric inner and outer balloons 11 and 13 is the leading end of a coaxial hose 17 formed of flexible synthetic plastic material, the rear ends of the balloons being clamped to the hose by O rings 15 and 16. Coaxially supported within hoses 17 is an inner pipe 18 of flexible plastic material which projects beyond the leading end of hose 17 into the tubular inner balloon 13. The projecting portion of pipe 18 is perforated to create a nozzle N from which a heated air stream is discharged into inner balloon 13.

Figure 3:
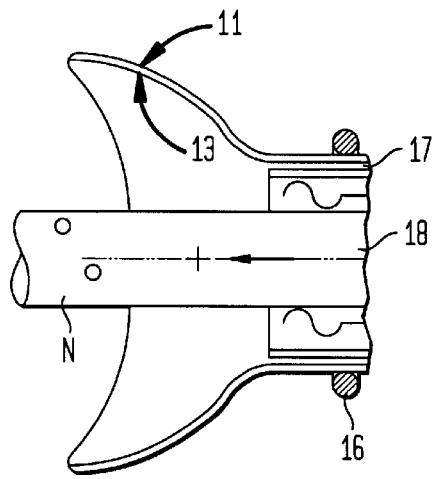
FIG. 3 is a partial view of the inner and outer balloons of the applicator in its inflated state.
Figure 4:
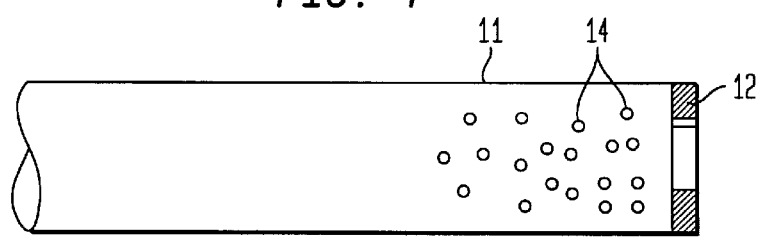
FIG. 4 illustrates the assembly of the inner and outer balloons.

Coaxial hose 17 which has a relatively long length couples applicator 10 to an external heated air source 21 which functions to pump a stream of heated air A into inner pipe 18, the stream being disclosed by nozzle N into inner balloon 13. The heated air stream which acts to inflate the inner balloon, as shown in FIGS. 2 and 3, is returned to source 21 through the annular flow passage V between outer hose 17 and its coaxial inner pipe 17. Thus the flow of heated air through the inner balloon is in a continuous circulating loop in which air temperature air is determined and controlled by source 21.

Heated air source 21 is preferably of the pulsatory wave type disclosed in the above identified Guibert patents. This air heat-energy wave is in a pulsatory heat pattern created by air pulses having high-temperature peaks and intervals between the pulses having a lower temperature. The temperature pattern of the stream inflating the inner balloon is such as to effect the transfer of heat to the surface of the tubular membrane being heated by the applicator to elevate the temperature of the cancerous lesions disrupting the surface to a level that is destructive of the lesions without raising the temperature of the surface which is free of lesions to a destructive level.

The diameter of applicator 10 in its uninflated state, as shown in FIG. 1, and of hose 17 extending extending therefrom is smaller than the internal diameter of the tubular membrane M into which applicator 10 is inserted. Hence even when, as in a colon, the tubular membrane therein has aa meandering path, it is not difficult to snake the applicator through the membrane to reach a site therein, as shown in FIG. 2, in which the surface of the membrane is disrupted by cancerous lesions.

When applicator 10 is at the desired site in membrane M, it is then put into operation by feeding a stream of heated air from source 21 into the inner balloon 13 which acts to inflate this balloon, as shown in FIGS. 2 and 3. The inflated inner balloon expands the perforated outer balloon 11 to cause it to conform to the surface of the membrane to be treated. Supply S of the chemotherapy agent surrounding the inner balloon is heated by the heated air flowing through the inner balloon.

This heated air preferably has a high relative humidity in order to increase the heat capacity of the atmosphere within the inner balloon. And in practice, the thermal conductivity of the inner balloon may be enhanced by dispersing in the latex of the inner balloon fine graphite or other thermally conductive particles.

Heat transferred from inner balloon 13 to the chemotherapy agent in supply S acts to heat and melt this anti-cancer agent to form a cream. And the pressure applied by the inner balloon to this cream acts to extrude it through holes H in outer balloon 11 which is expanded to conform to the surface of the membrane M. This extrusion causes the heated cream to coat the lesions on the surface of the membrane.

The heated chemotherapy coating on the lesion serves two functions. The first is hyperthermic which elevates the temperature of the cancerous lesions to a level which is destructive thereof. These chemo and thermo actions are synergistic in nature, for the hyperthermia acts to elevate the temperature of the cream and enhance its effectiveness as a chemotherapy agent to destroy the lesions.

To maintain the heated circulating air stream at a desired temperature level, a thermister 22 or other heat sensor is disposed in the return passage V in the coaxial hose 17, sensor 22 yielding a signal that depends on the temperature of the air stream passing through this passage. This signal is applied to an electronic controller 23 having an adjustable set point. Controller 23 compares the signal with the set point to determine the extent to which the temperature of the stream deviates from the set point and acts to yield a control signal which is applied to the heated air source to adjust the temperature of the air stream so that it is at the desired set point temperature level.

The embodiment of the applicator illustrated in the drawing is a chemo-thermo applicator, for it synergistically combines a hyperthermia anti-cancer action with a chemotherapy anti-cancer action.

In practice, the applicator can be simplified to provide only a hyperthermia action. In that event, the applicator only includes a single tubular balloon which is insertable into a tubular membrane in the body of an individual to a site at which the surface of the membrane is disrupted by cancerous lesions. The single balloon is then inflated by heated air to conform to this surface and to transfer heat to the surface to destroy the lesions.

While there has been disclosed preferred embodiments of a chemo-thermo applicator in accordance with the invention, it will be appreciated that many changes may be made therein without departing from the spirit of the invention.

We claim:

1. An applicator insertable into a tubular membrane in the body of an individual to occupy a site therein at which the surface of the membrane is disrupted by cancerous lesions, the applicator comprising:

A. an inner tubular balloon which normally has a diameter smaller than that of the membrane whereby the applicator can travel through the membrane to said site and an outer, porous, tubular balloon disposed over the inner balloon and having a diameter smaller than that of the membrane; and B. means to feed a heated air stream into the balloon to inflate the inner balloon and cause it to expand, the heat of the air stream effective to soften a composition disposed between the inner and outer balloons and the expansion of the inner balloon effective to dispense said softened composition through the openings in the outer balloon, said expansion also causing the balloons to conform to the surface of the membrane and apply heat thereto and transfer heat from said heated air stream to said lesions acting to raise the temperature of the lesions to a level destructive of the lesions.

2. An applicator as set forth in claim 1, in which the applicator is coupled to the inner balloon by a coaxial hose having an inner pipe to a source of heated air which pumps a stream of heated air through said pipe to said inner balloon and returns the stream from the balloon to said source through an annular passage between the pipe and the hose.

3. An applicator as set forth in claim 1, in which the air stream has a pulsatory pattern formed by periodic pulses having a relatively high peak temperature and intervals therebetween having a lower temperature.

4. A chemo-thermo applicator insertable into a tubular membrane in the body of an individual in which the surface of the membrane at a site therein is disrupted by cancerous lesions, the applicator comprising:

A. concentrical tubular outer and inner balloons, the outer balloon being perforated and having a diameter smaller than that of the membrane whereby the applicator can travel through the membrane to said site, said concentrical outer and inner balloons defining an annular space therebetween;

B. a chemotherapetutic agent filling said space formed of a pharmaceutical which when heated, assumes a cream form;

C. a source of heated air; and

D. means coupled to said source to feed a stream of heated air into the inner balloon to inflate it and to heat and melt the chemotherapy agent in the space surrounding the inner balloon to form a cream, inflation of the inner balloon causing the outer balloon to expand against the surface of the membrane and causing the cream to be extruded through the perforations of the outer balloon to coat the lesions with a heated cream which raises the temperature of the lesions to a level destructive thereof.

5. An applicator as set forth in claim 4, in which the means coupling the applicator to the source is a coaxial hose having an inner pipe and an annular flow passage between the pipe and the hose, the stream of heated air from the source flowing into the inner balloon through said pipe, and being returned therefrom to said source through said annular passage.

6. An applicator as set forth in claim 5, having a first disc bonded to the front end of the inner balloon and a second disc bonded to the front end of the outer balloon said first disc and said second disc being joined together by a nose piece.

7. An application as set forth in claim 6, in which the leading end of the hose is telescoped into the rear ends of the concentric balloons and is clamped thereto.

8. An applicator as set forth in claim 7, in which the pipe extends beyond the leading end of the hose into said inner balloon and is perforated to form a nozzle for discharging heated air into the inner balloon.

9. An applicator as set forth in claim 5, further including means to sense the temperature of the air flowing in said annular passage to produce a signal for operating a controller to regulate the temperature of said source.

* * * * *